(12) United States Patent
Rubinsky et al.

(10) Patent No.: US 7,718,409 B2
(45) Date of Patent: *May 18, 2010

(54) CONTROLLED ELECTROPORATION AND MASS TRANSFER ACROSS CELL MEMBRANES

(75) Inventors: Boris Rubinsky, Milpitas, CA (US); Yong Huang, Milpitas, CA (US)

(73) Assignee: The Regents of the University of California, Oakland, CA (US)

(*) Notice: Subject to any disclaimer, the term of this patent is extended or adjusted under 35 U.S.C. 154(b) by 335 days.

This patent is subject to a terminal disclaimer.

(21) Appl. No.: 11/340,176

(22) Filed: Jan. 25, 2006

(65) Prior Publication Data

US 2006/0121610 A1    Jun. 8, 2006

Related U.S. Application Data

(63) Continuation of application No. 10/407,580, filed on Apr. 3, 2003, now abandoned, which is a continuation of application No. 09/863,117, filed on May 22, 2001, now Pat. No. 6,562,604, which is a continuation of application No. 09/358,510, filed on Jul. 21, 1999, now Pat. No. 6,300,108.

(51) Int. Cl.
*C12N 13/00* (2006.01)
*C12N 15/01* (2006.01)
*C12N 15/87* (2006.01)

(52) U.S. Cl. .............. 435/173.6; 435/173.1; 435/446; 435/459

(58) Field of Classification Search .............. None
See application file for complete search history.

(56) References Cited

U.S. PATENT DOCUMENTS

| | | |
|---|---|---|
| 1,653,819 A | 12/1927 | Northcott et al. |
| 4,016,886 A | 4/1977 | Doss |
| 4,226,246 A | 10/1980 | Fragnet |
| 4,262,672 A | 4/1981 | Kief |
| 4,407,943 A | 10/1983 | Cole et al. |
| 4,810,963 A | 3/1989 | Blake-Coleman et al. |
| 4,907,601 A | 3/1990 | Frick |
| 4,946,793 A | 8/1990 | Marshall, III |
| 5,019,034 A | 5/1991 | Weaver et al. |
| 5,052,391 A | 10/1991 | Silberstone et al. |
| 5,058,605 A | 10/1991 | Slovak |
| 5,098,843 A | 3/1992 | Calvin |
| 5,134,070 A | 7/1992 | Casnig |
| 5,173,158 A | 12/1992 | Schmukler |
| 5,193,537 A | 3/1993 | Freeman |
| 5,273,525 A | 12/1993 | Hofmann |
| 5,283,194 A | 2/1994 | Schmukler |
| 5,318,563 A | 6/1994 | Malis et al. |
| 5,328,451 A | 7/1994 | Davis et al. |
| 5,389,069 A | 2/1995 | Weaver |
| 5,403,311 A | 4/1995 | Abele et al. |
| 5,425,752 A | 6/1995 | Vu'Nguyen |
| 5,439,440 A | 8/1995 | Hofmann |
| 5,458,625 A | 10/1995 | Kendall |
| 5,533,999 A | 7/1996 | Hood et al. |
| 5,536,240 A | 7/1996 | Edwards et al. |
| 5,575,811 A | 11/1996 | Reid et al. |
| 5,626,146 A | 5/1997 | Barber et al. |
| 5,634,899 A | 6/1997 | Shapland et al. |
| 5,674,267 A | 10/1997 | Mir et al. |
| 5,702,359 A | 12/1997 | Hofmann |
| 5,720,921 A | 2/1998 | Meserol |

(Continued)

FOREIGN PATENT DOCUMENTS

DE    863111    1/1953

(Continued)

OTHER PUBLICATIONS

Coates, C.W., et al. "The Electric Discharge of the Electric Eel, Electrophorous electricus" Zoologica. 1937, 22(1), pp. 1-32 (Abstract only).*

(Continued)

*Primary Examiner*—Christopher R Tate
*Assistant Examiner*—Aaron J Kosar
(74) *Attorney, Agent, or Firm*—Karl Bozicevic; Bozicevic, Field & Francis LLP

(57) ABSTRACT

Electroporation is performed in a controlled manner in either individual or multiple biological cells or biological tissue by monitoring the electrical impedance, defined herein as the ratio of current to voltage in the electroporation cell. The impedance detects the onset of electroporation in the biological cell(s), and this information is used to control the intensity and duration of the voltage to assure that electroporation has occurred without destroying the cell(s). This is applicable to electroporation in general. In addition, a particular method and apparatus are disclosed in which electroporation and/or mass transfer across a cell membrane are accomplished by securing a cell across an opening in a barrier between two chambers such that the cell closes the opening. The barrier is either electrically insulating, impermeable to the solute, or both, depending on whether pore formation, diffusive transport of the solute across the membrane, or both are sought. Electroporation is achieved by applying a voltage between the two chambers, and diffusive transport is achieved either by a difference in solute concentration between the liquids surrounding the cell and the cell interior or by a differential in concentration between the two chambers themselves. Electric current and diffusive transport are restricted to a flow path that passes through the opening.

7 Claims, 4 Drawing Sheets

U.S. PATENT DOCUMENTS

| | | | |
|---|---|---|---|
| 5,778,894 A | 7/1998 | Dorogi et al. |
| 5,782,882 A | 7/1998 | Lerman et al. |
| 5,800,378 A | 9/1998 | Edwards et al. |
| 5,810,762 A | 9/1998 | Hofmann |
| 5,836,905 A | 11/1998 | Lemelson et al. |
| 5,843,026 A | 12/1998 | Edwards et al. |
| 5,873,849 A | 2/1999 | Bernard |
| 5,919,142 A | 7/1999 | Boone et al. |
| 5,947,889 A | 9/1999 | Hehrlein |
| 5,983,131 A | 11/1999 | Weaver et al. |
| 5,991,697 A | 11/1999 | Nelson et al. |
| 5,999,847 A | 12/1999 | Elstrom |
| 6,009,347 A | 12/1999 | Hofmann |
| 6,010,613 A | 1/2000 | Walters et al. |
| 6,016,452 A | 1/2000 | Kasevich |
| 6,041,252 A | 3/2000 | Walker et al. |
| 6,055,453 A | 4/2000 | Hofmann et al. |
| 6,068,650 A | 5/2000 | Hofmann et al. |
| 6,085,115 A | 7/2000 | Weaver et al. |
| 6,090,106 A | 7/2000 | Goble et al. |
| 6,102,885 A | 8/2000 | Bass |
| 6,106,521 A | 8/2000 | Blewett et al. |
| 6,109,270 A | 8/2000 | Mah et al. |
| 6,122,599 A | 9/2000 | Mehta |
| 6,132,419 A | 10/2000 | Hofmann |
| 6,159,163 A | 12/2000 | Strauss et al. |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann |
| 6,219,577 B1 | 4/2001 | Brown et al. |
| 6,241,702 B1 | 6/2001 | Lundquist et al. |
| 6,261,831 B1 | 7/2001 | Agee |
| 6,278,895 B1 | 8/2001 | Bernard |
| 6,300,108 B1 | 10/2001 | Rubinsky et al. ......... 435/173.6 |
| 6,326,177 B1 | 12/2001 | Schoenbach et al. |
| 6,347,247 B1 | 2/2002 | Dev et al. |
| 6,349,233 B1 | 2/2002 | Adams |
| 6,351,674 B2 | 2/2002 | Silverstone |
| 6,387,671 B1 | 5/2002 | Rubinsky |
| 6,403,348 B1 | 6/2002 | Rubinsky |
| 6,470,211 B1 * | 10/2002 | Ideker et al. ................ 607/5 |
| 6,482,619 B1 | 11/2002 | Rubinsky |
| 6,493,592 B1 | 12/2002 | Leonard et al. |
| 6,500,173 B2 | 12/2002 | Underwood et al. |
| 6,526,320 B2 | 2/2003 | Mitchell |
| 6,562,604 B2 | 5/2003 | Rubinsky |
| 6,607,529 B1 | 8/2003 | Jones et al. |
| 6,611,706 B2 | 8/2003 | Avrahami et al. |
| 6,613,211 B1 | 9/2003 | McCormick et al. |
| 6,627,421 B1 | 9/2003 | Unger et al. |
| 6,653,091 B1 | 11/2003 | Dunn et al. |
| 6,669,691 B1 | 12/2003 | Taimisto |
| 6,692,493 B2 | 2/2004 | McGovern et al. |
| 6,697,670 B2 | 2/2004 | Chomenky et al. |
| 6,702,808 B1 | 3/2004 | Kreindel |
| 6,795,728 B2 | 9/2004 | Chomenky et al. |
| 6,801,804 B2 | 10/2004 | Miller et al. |
| 6,865,416 B2 | 3/2005 | Dev et al. |
| 6,892,099 B2 | 5/2005 | Jaafar et al. |
| 6,912,417 B1 | 6/2005 | Bernard et al. |
| 6,927,049 B2 | 8/2005 | Rubinsky |
| 6,962,587 B2 | 11/2005 | Johnson et al. |
| 6,972,014 B2 | 12/2005 | Eum et al. |
| 6,994,706 B2 | 2/2006 | Chornenky et al. |
| 7,053,063 B2 | 5/2006 | Rubinsky |
| 7,063,698 B2 | 6/2006 | Whayne et al. |
| 7,130,697 B2 | 10/2006 | Chornenky et al. |
| 7,211,083 B2 | 5/2007 | Chornenky et al. |
| 7,267,676 B2 | 9/2007 | Chornenky et al. |
| 2001/0044596 A1 | 11/2001 | Jaafar |
| 2002/0010491 A1 | 1/2002 | Schoenbach |
| 2002/0055731 A1 | 5/2002 | Atala et al. |
| 2002/0077676 A1 | 6/2002 | Schroeppel et al. |
| 2002/0099323 A1 | 7/2002 | Dev et al. |
| 2002/0138117 A1 | 9/2002 | Son |
| 2002/0193831 A1 | 12/2002 | Smith, III |
| 2003/0009110 A1 | 1/2003 | Tu et al. |
| 2003/0060856 A1 | 3/2003 | Chornenky et al. |
| 2003/0088189 A1 | 5/2003 | Tu et al. |
| 2003/0130711 A1 | 7/2003 | Pearson et al. |
| 2003/0170898 A1 | 9/2003 | Gundersen et al. |
| 2003/0208200 A1 | 11/2003 | Palanker et al. |
| 2003/0225360 A1 | 12/2003 | Eppstein et al. |
| 2004/0019371 A1 | 1/2004 | Jaafar et al. |
| 2004/0059389 A1 | 3/2004 | Chornenky et al. |
| 2004/0146877 A1 | 7/2004 | Diss et al. |
| 2004/0153057 A1 | 8/2004 | Davison |
| 2004/0243107 A1 | 12/2004 | Mackoviak |
| 2004/0267189 A1 | 12/2004 | Mavor et al. |
| 2005/0043726 A1 | 2/2005 | McHale et al. |
| 2005/0049541 A1 | 3/2005 | Behar et al. |
| 2005/0165393 A1 | 7/2005 | Eppstein |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0261672 A1 | 11/2005 | Deem et al. |
| 2005/0288730 A1 | 12/2005 | Deem et al. |
| 2006/0015147 A1 | 1/2006 | Persson et al. |
| 2006/0025760 A1 | 2/2006 | Podhajsky |
| 2006/0079883 A1 | 4/2006 | Elmouelhi et al. |
| 2006/0121610 A1 | 6/2006 | Rubinsky et al. |
| 2006/0212078 A1 | 9/2006 | Demarais et al. |
| 2006/0217703 A1 | 9/2006 | Chornenky et al. |
| 2006/0264752 A1 | 11/2006 | Rubinsky et al. |
| 2007/0043345 A1 | 2/2007 | Davalos et al. |
| 2007/0118069 A1 | 5/2007 | Persson et al. |
| 2008/0052786 A1 | 2/2008 | Lin et al. |

FOREIGN PATENT DOCUMENTS

| | | |
|---|---|---|
| DE | 4000893 | 7/1991 |
| EP | 0378132 | 7/1990 |
| EP | 0935482 | 5/2005 |
| WO | 9639531 | 12/1996 |
| WO | 0020554 | 4/2000 |
| WO | 0107584 | 2/2001 |
| WO | 0107585 | 2/2001 |
| WO | WO 01/07583 | 2/2001 |
| WO | 0181533 | 11/2001 |
| WO | 2004037341 | 5/2004 |

OTHER PUBLICATIONS

Rols, M.P., et al. "Highly Efficient Transfection of Mammalian Cells by Electric Field Pulses: Application to Large volumes of Cell Culture by Using a Flow System" Eur. J. Biochem. 1992, 206, pp. 115-121.*

Andreason, G.L. (1993) *J. Tiss. Cult. Meth.*, 15:56-62.

Barber, *Advances in Biomedical Engineering*, J.E.W. W. Beneken and V. Thevenin (eds) IOS Press pp. 165-173 (1993).

Cook et al., *IEEE Transactions on Biomedical Engineering*, 41(6):713-722 (Aug. 1994).

Duraiswami et al., *Engineering and Analysis with Boundary Elements*, 22:13-31 (1998).

Duraiswami et al., *Chemical Engineering Science*, 32(13):2185-2196 (1997).

Duraiswami et al., *Bounary Element Technology XII*, pp. 226-237 (1997).

Gencer et al., *IEEE Transactions on Biomedical Engineering*, 43(2):139-149 (Feb. 1996).

Gilbert et al., *Biochimica et Biophysica Act*, 1334:9-14 (1997).

Griffiths et al., *Phys. Med. Biol.*, 34(10):1465-1476 (Oct. 1989).

Griffiths et al., *IEEE Transactions on Biomedical Engineering*, 42:948-954 (1995).

Griffiths et al., *Phys. Med. Biol.*, 32(11):1435-1444 (1987).
Glidewell et al., *Biomed Sci Instrum*, 29:251-257 (1993).
Hapala, I. (1997) *Critical Reviews in Biotechnology*, 17:105-122.
Heller et al., *Advanced Drug Delivery Reviews*, 35:119-129 (1999).
Ho, S.Y. and Mittal, G.S. (1996) *Critical Reviews in Biotechnology*, 16:349-362.
Holder et al., *Proceedings of the X. International Conference on Electrical Bioimpedance*, pp. 512-519 (1997).
Hughes et al., *Physiol. Meas.*, 15:A199-A209 (1994).
Jaroszeski et al., *Advanced Drug Delivery Reviews*, 35:131-137 (1999).
Liu et al., *Clin. Phys. Physiol. Meas.*, 13(Suppl. A):197-200 (1992).
Lundquist, J.A. et al. (1998) *Proc. Natl. Acad. Sci USA*, 95:10356-10360.
Lurquin, P.F. (1997) *Molecular Biotechnology*, 7:5-35.
Mir et al., *Cancerology*, 313(III):613-618 (1991).
Narayan, P. and Dahiya, R. (1992) *J. Urol.*, 148:1600-1604.
Neuman, E. et al. (1982) *EMBO J*, 7:841-845.
Sharma et al., *Biophysical Journal*, vol. 71:3229-3241 (1996).
Weaver, J.C. (1993) *Journal of Cellular Biochemistry*, 51:426-435.
Blad et al., "Impedance spectra of tumour tissue in comparison with normal tissue; a possible clinical application for electrical impedance tomography" *Physiol Meas* 17:A105-A115 (1996).
Amasha et al., Clin Phys. Physiol Meas, 9:49-53 (1988).
Beneken and Thevenia (eds) IOS Press pp. 165-173 (1993).
Blad et al., Physiol Meas., 17:A105-A115 (1996).
Brown et al., Clin Phys Physiol Meas, 13:175-179 (1992).
Crowly, Biophysical Journal, 13:711-724 (1973).
Davalos et al., IEEE Transactions on Biomedical Engineering, 49(4):400-403 (Apr. 2002).
Davalos et al., Annals of Biomedical Engineering 33(2):223-231 (Feb. 2005).
Dean et al., Am. J. Physiol. Cell Physiol., 289:233-235 (2005).
Dev et al., IEEE Transactions of Plasma Science, 28(1):206-223 (Feb. 2000).
Erez et al., J. Biomech. Eng., 102(1):42-9 (1980).
Gehl et al., Biochimica et Biophysica Acta, 1428:233-240 (1999).
Gothelf et al., Cancer Treatment Reviews, 29:371-387 (2003).
Ivanusa et al., Radiol Oncol., 35(2):139-147 (2001).
Kinosita et al., PNAS, 74(5):1923-1927 (May 1977).
Lynn et al., J. Gen. Physiol, 26:179-93 (1942).
Miklavcic et al., Biophysical Journal, 74:2152-2158 (May 1998).
Miklavcic et al., Biochimica et Biophysica Acta, 1523:73-73 (2000).
Mir et al., European Journal of Cancer, 27:68-72 (1991).
Mir et al., British Journal of Cancer, 77(12):2336-2342 (1998).
Neumann et al., J. Membrane Biol., 10:279-290 (1972).
Okino et al., Japanese Journal of Cancer Resesarch, 78(12):1319-21 (1987).
Sersa et al., Br. J. Cancer, 87(9):1047-54 (2002).
Sersa et al., Oncol., 37(1):43-8 (2003).
Zimmerman et al., Biophysical Journal, 14(11):881-889 (1974).
Baker, et al., Calcium-Dependent Exocytosis in Bovine Adrenal Medullary Cells with Leaky Plasma Membranes, *Nature*, vol. 276, pp. 620-622, 1978.
Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.
Bown, S.G., Phototherapy of tumors. *World J. Surgery*, 1983. 7: p. 700-9.
BPH Management Strategies: Improving Patient Satisfaction, *Urology Times*, May 2001, vol. 29, Supplement 1.
Coates, C.W.,et al., "The Electrical Discharge of the Electric Eel, Electrophorous Electricus," Zoologica, 1937, 22(1), pp. 1-32.
Cowley, Good News for Boomers, *Newsweek*, Dec. 30, 1996/Jan. 6, 1997.
Cox, et al., Surgical Treatment of Atrial Fibrillation: A Review, *Europace* (2004) 5, S20-S-29.
Davalos, et al., Theoretical Analysis of the Thermal Effects During In Vivo Tissue Electroporation, Bioelectrochemistry, vol. 61, pp. 99-107, 2003.
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002, 253 pages.
Dev, et al., Sustained Local Delivery of Heparin to the Rabbit Arterial Wall with an Electroporation Catheter, *Catheterization and Cardiovascular Diagnosis*, Nov. 1998, vol. 45, No. 3, pp. 337-343.
Edd, J., et al., In-Vivo Results of a New Focal Tissue Ablation Technique: Irreversible Electroporaton, *IEEE Trans. Biomed. Eng.* 53 (2006) p. 1409-1415.
Foster, R.S., et al., High-intensity focused ultrasound in the treatment of prostatic disease. *Eur. Urol.*, 1993. 23: 44-7).
Gauger, et al., A Study of Dielectric Membrane Breakdown in the Fucus Egg, *J. Membrane Biol.*, vol. 48, No. 3, pp. 249-264, 1979.
Gilbert, et al., The Use of Ultrasound Imaging for Monitoring Cryosurgery, Proceedings 6th Annual Conference, IEEE Engineering in Medicine and Biology, 107-111, 1984.
Huang, et al., Micro-Electroporation: Improving the Efficiency and Understanding of Electrical Permeabilization of Cells, *Biomedical Microdevices*, vol. 2, pp. 145-150, 1999.
Issa, et al., The TUNA Procedure for BPH: Review of the Technology: The TUNA Procedure for BPH: Basic Procedure and Clinical Results, Reprinted from *Infections in Urology*, Jul./Aug. 1998 and Sep./Oct. 1998, 16 pages.
Miller, L., et al., Cancer cells ablation with irreversible electroporation, *Technology in Cancer Research and Treatment* 4 (2005) 699-706.
Mir, Therapeutic Perspectives of In Vivo Cell Electropermeabilization, *Bioelectrochemistry*, vol. 53, pp. 1-10, 2000.
Mir, L.M., et al., Electric Pulse-Mediated Gene Delivery to Various Animal Tissues, in Advances in Genetics, Academic Press, 2005, p. 83-114.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Naslund, Michael J., Transurethral Needle Ablation of the Prostate, *Urology*, vol. 50, No. 2, Aug. 1997, pp. 167-172.
Naslund, Cost-Effectiveness of Minimally Invasive Treatments and Transurethral Resection (TURP) in Benign Prostatic Hyperplasia (BPH), (Abstract), Presented at 2001 AUA National Meeting Anaheim,, CA, Jun. 5, 2001, 1 page.
Neumann, et al., Gene Transfer into Mouse Lyoma Cells by Electroporation in High Electric Fields, *J. Embo.*, vol. 1, No. 7, pp. 841-845, 1982.
Onik, et al., Sonographic Monitoring of Hepatic Cryosurgery in an Experimental Animal Model, *AJR American J. of Roentgenology*, vol. 144, pp. 1043-1047, May 1985.
Onik, et al., Ultrasonic Characteristics of Frozen Liver, *Cryobiology*, vol. 21, pp. 321-328, 1984.
Organ, L.W., Electrophysiological principles of radiofrequency lesion making, *Apply. Neurophysiol.*, 1976. 39: p. 69-76.
Piñero, et al., Apoptotic and Necrotic Cell Death Are Both Induced by Electroporation in HL60 Human Promyeloid Leukaemia Cells, *Apoptosis*, vol, 2, No. 3, 330-336, Aug. 1997.
Precision Office Tuna System, When Patient Satisfaction is Your Goal, 2001, 11 pages.
Rols, M.P., et al., Highly Efficient Transfection of Mammalian Cells by Electric Field Pulses: Application to Large Volumes of Cell Culture by Using a Flow System, *Eur. J. Biochem.* 1992, 206, pp. 115-121.
Rubinsky, B., ed, Cryosurgery. *Annu Rev. Biomed. Eng.* vol. 2 2000. 157-187.
Shiina, S., et al, Percutaneous ethanol injection therapy for hepatocellular carcinoma: results in 146 patients. *AJR*, 1993, 160: p. 1023-8.
Thompson, et al., To determine whether the temperature of 2% lignocaine gel affects the initial discomfort which may be associated with its instillation into the male urethra, *BJU International* (1999), 84, 1035-1037.

VIDAMED, Inc., Transurethral Needle Ablation (TUNA): Highlights from Worldwide Clinical Studies, Vidamed's Office TUNA System, 2001, 4 pages.

Weaver, et al., Theory of Electroporation: A Review, *Bioelectrochemistry and Bioenergetics*, vol. 41, pp. 136-160, 1996.

Zlotta, et al., Possible Mechanisms of Action of Transurethral Needle Ablation of the Prostate on Benign Prostatic Hyperplasia Symptoms: a Neurohistochemical Study, Reprinted from *Journal of Urology*, vol. 157, No. 3, Mar. 1997, pp. 894-899.

Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001, 1 page.

\* cited by examiner

CONTROLLED ELECTROPORATION AND MASS TRANSFER ACROSS CELL MEMBRANES

CROSS REFERENCES

This application is a continuation of our earlier filed application Ser. No. 10/407,580 filed Apr. 3, 2003, which is a continuation of our earlier filed application Ser. No. 09/863,117 filed May 22, 2001 (issued as U.S. Pat. No. 6,562,604 on May 13, 2003), which application is a continuation of our earlier filed application Ser. No. 09/358,510 filed Jul. 21, 1999 (issued as U.S. Pat. No. 6,300,108 on Oct. 9, 2001), which applications are incorporated herein by reference and to which applications we claim priority under 35 USC §120.

This invention resides in the fields of electroporation and mass transfer across cell membranes.

BACKGROUND OF THE INVENTION

Electroporation is a technique that is used for introducing chemical species into biological cells, and is performed by exposing the cells to an electric potential that traverses the cell membrane. While its mechanism is not fully understood, electroporation is believed to involve the breakdown of the cell membrane lipid bilayer leading to the formation of transient or permanent pores in the membrane that permit the chemical species to enter the cell by diffusion. The electric potential is typically applied in pulses, and whether the pore formation is reversible or irreversible depends on such parameters as the amplitude, length, shape and repetition rate of the pulses, in addition to the type and development stage of the cell. As a method of introducing chemical species into cells, electroporation offers numerous advantages: it is simple to use; it can be used to treat whole populations of cells simultaneously; it can be used to introduce essentially any macromolecule into a cell; it can be used with a wide variety of primary or established cell lines and is particularly effective with certain cell lines; and it can be used on both prokaryotic and eukaryotic cells without major modifications or adaptations to cell type and origin. Electroporation is currently used on cells in suspension or in culture, as well as cells in tissues and organs.

Electroporation is currently performed by placing one or more cells, in suspension or in tissue, between two electrodes connected to a generator that emits pulses of a high-voltage electric field. The pore formation, or permealization, of the membrane occurs at the cell poles, which are the sites on the cell membranes that directly face the electrodes and thus the sites at which the transmembrane potential is highest. Unfortunately, the degree of permealization occurring in electroporation varies with the cell type and also varies among cells in a given population. Furthermore, since the procedure is performed in large populations of cells whose properties vary among the individual cells in the population, the electroporation conditions can only be selected to address the average qualities of the cell population; the procedure as currently practiced cannot be adapted to the specific characteristics of individual cells. Of particular concern is that under certain conditions, electroporation can induce irreversible pore formation and cell death. A high electric field, for example, may thus produce an increase in transfection efficiency in one portion of a cell population while causing cell death in another. A further problem with known methods of electroporation is that the efficiency of transfection by electroporation can at times be low. In the case of DNA, for example, a large amount of DNA is needed in the surrounding medium to achieve effective transformation of the cell.

Many of the problems identified above are a consequence of the fact that the process of electroporation in both individual cells and tissues cannot be controlled in real time. There are no means at present to ascertain in real time when a cell enters a state of electroporation. As a result, the outcome of an electroporation protocol can only be determined through the eventual consequences of the mass transfer process and its effect on the cell. These occur long after the mass transfer under electroporation has taken place. These and other deficiencies of current methods of electroporation are addressed by the present invention.

Also relevant to the present invention are current techniques for the study and control of mass transfer across cell membranes. Knowledge of mass transfer across cell membranes in nature, both in cells that are functioning normally and in diseased cells, is valuable in the study of certain diseases. In addition, the ability to modify and control mass transfer across cell membranes is a useful tool in conducting research and therapy in modern biotechnology and medicine. The introduction or removal of chemical species such as DNA or proteins from the cell to control the function, physiology, or behavior of the cell provides valuable information regarding both normal and abnormal physiological processes of the cell.

The most common method of effecting and studying mass transfer across a cell membrane is to place the cell in contact with a solution that contains the compound that is to be transported across the membrane, either with or without electroporation. This bulk transfer method does not permit precise control or measurement of the mass transfer across the membrane. The composition of the solution at specific sites is not known and is variable. In addition, when an electric field is present, the local field intensity will vary from one point to another. Furthermore, the surface of the cell that is exposed to the solution is not well defined. Cell surface areas vary among cells in a given population, and this leads to significant differences among the cells in the amount of mass transfer. For these reasons, the amount of mass transfer achieved by bulk transfer processes is not uniform among cells, and the actual amount transferred for any particular cell cannot be determined.

Attempts made so far to overcome the limitations of bulk transfer techniques include techniques for treating individual cells that include either the mechanical injection (microinjection) of chemical compounds through the cell membrane or electroporation with microelectrodes. In injection techniques, the membrane is penetrated with a needle to deliver a chemical agent, localizing the application of the chemical agent to a small region close to the point of injection. This requires manipulation of the cell with the human hand, a technique that is difficult to perform, labor-intensive, and not readily reproducible. Electroporation with microelectrodes suffers these problems as well as the lack of any means to detect the onset of electroporation in an individual cell. These problems are likewise addressed by the present invention.

SUMMARY OF THE INVENTION

The present invention arises in part from the discovery that the onset and extent of electroporation in a biological cell can be correlated to changes in the electrical impedance (which term is used herein to mean the ratio of current to voltage) of the biological cell or of a conductive medium that includes the biological cell. An increase in the current-to-voltage ratio across a biological cell occurs when the cell membrane becomes permeable due to pore formation. Likewise, a decrease in the current-to-voltage ratio through a flowing conductive fluid occurs when the fluid draws a biological cell into the region between the electrodes in a flow-through electric cell. Thus, by monitoring the impedance of the biological cell or of an electrolyte solution in which the cell is suspended, one can detect the point in time in which pore formation in the cell membrane occurs, as well as the relative degree of cell membrane permeability due to the pore formation. This information can then be used to establish that a given cell has in fact undergone electroporation, or to control the electroporation process by governing the selection of the voltage magnitude. This discovery is also useful in the simultaneous electroporation of multitudes of cells, since it provides a direct indication of the actual occurrence of electroporation and an indication of the degree of electroporation averaged over the multitude. The discovery is likewise useful in the electroporation of biological tissue (masses of biological cells with contiguous membranes) for the same reasons.

The benefits of this process include a high level of control over the onset and degree of electroporation, together with a more detailed knowledge of the occurrence and degree of permeability created in particular individual cells or cell masses. When applied to individual cells or to a succession of individual cells, this process assures that the individual cells are indeed rendered permeable and are indeed transformed by the introduction of chemical species. The process also offers the ability to increase the efficiency of electroporation by avoiding variations in the electrical environment that would destroy some cells while having an insufficient effect on others.

In some of its more specific embodiments, the present invention involves the use of an electrical cell in which a biological cell can be placed and that contains a barrier that directs the electric current flow and hence the ion flow through a flow path that passes through the biological cell while permitting substantially no electric current to bypass the biological cell. In some of these embodiments, the invention involves the use of an apparatus containing two liquid-retaining chambers separated by a barrier that is substantially impermeable to an electric current. The barrier contains an opening that is smaller than the biological cell such that the biological cell once lodged in the opening will plug or close the opening. To achieve electroporation, the biological cell is secured over the opening by mechanical or chemical means, preferably in a reversible manner so that the biological cell can later be removed without damage to the biological cell. Once the biological cell is secured over the opening, a voltage is imposed between the two chambers and across the biological cell residing in the opening. The passage of current between the chambers is thus restricted to a path passing through the opening and hence through the biological cell. By monitoring the current-voltage relation in the electric cell, the onset of electroporation is detected and the degree of pore formation is controlled, to both assure that electroporation is occurring and to prevent excessive pore formation and cell death. The user is thus afforded a highly precise knowledge and control of the condition of and the flux across the biological cell membrane.

In another series of embodiments, this invention is useful in the diffusive transport of chemical species into or out of a biological cell. In these embodiments, the cell is again divided into two chambers separated by a barrier, and the biological cell is lodged across an opening in the barrier in such a manner that the passage of liquid around the cell from one chamber to the other is substantially prevented. A liquid solution of the species to be introduced into the biological cell is placed in one or both of the chambers. The concentration of the species in the solution differs from that in the cell (either higher or lower, depending on whether one seeks to introduce or remove the species from the cell), or the concentration in one chamber differs from that in the other chamber.

In preferred methods of applying this invention to diffusive transport, the solutions in the two chambers differ in concentration such that the driving force for the diffusive transport is between the two chambers themselves rather than between the chambers and the interior of the biological cell. Knowledge and controlled monitoring of the concentrations in each of the two chambers on a periodic or continuous basis as the diffusion proceeds, together with the precise knowledge of the dimensions of the opening, enables the user to precisely observe and control the rate and amount of the species that enters the cell. The diffusion time can be controlled by imposing stepwise changes in the concentrations in either or both of the chambers, thereby imposing or removing the concentration differential. An application of particular interest is the combination of this type of diffusive transport of a chemical species with controlled electroporation as described in the preceding paragraph.

Each of the various embodiments of this invention may be used with two or more biological cells simultaneously, or cell masses such as in tissue, rather than just one cell. The apparatus described above can be adapted for use with two or more biological cells by arranging the barrier such that the current or diffusive transport will be restricted to a flow path that passes through all of the cells while preventing bypass around the cells. A further application of the concepts of this invention is the electroporation of biological cells suspended in a flowing liquid. Electrodes are placed in fixed positions in the flow channel, and a voltage is imposed between the electrodes while current passing between the electrodes is monitored. Biological cells entering the region between the electrodes will lower the current, the impedance serving as an indication of the presence of one or more cells in the region, and optionally also as a signal to initiate the application of a higher voltage sufficient to achieve electroporation.

Among the advantages that this invention offers relative to the prior art are the ability to treat cells individually and to adapt the treatment conditions to the needs of individual cells. In embodiments where voltage is applied, the monitoring of the impedance affords the user knowledge of the presence or absence of pores and shows the progress of the pore formation and whether irreversible pore formation that might lead to cell death has occurred. An advantage of the barrier-and-opening apparatus is its highly efficient use of electrical energy by virtue of its restriction of the current to a current flow path passing through the opening. A still further advantage is the ability of the apparatus and method to be integrated into an automated system whereby the condition of each cell is monitored by instrumentation and individual cells are lodged in the opening and then removed at times governed by the monitored conditions.

These and further features, advantages and objects of the invention will be better understood from the description that follows.

BRIEF DESCRIPTION OF THE DRAWINGS

FIG. 3b is a transverse cross section of the device shown in FIG. 3a.

DESCRIPTION OF THE INVENTION AND SPECIFIC EMBODIMENTS

Figure 1:
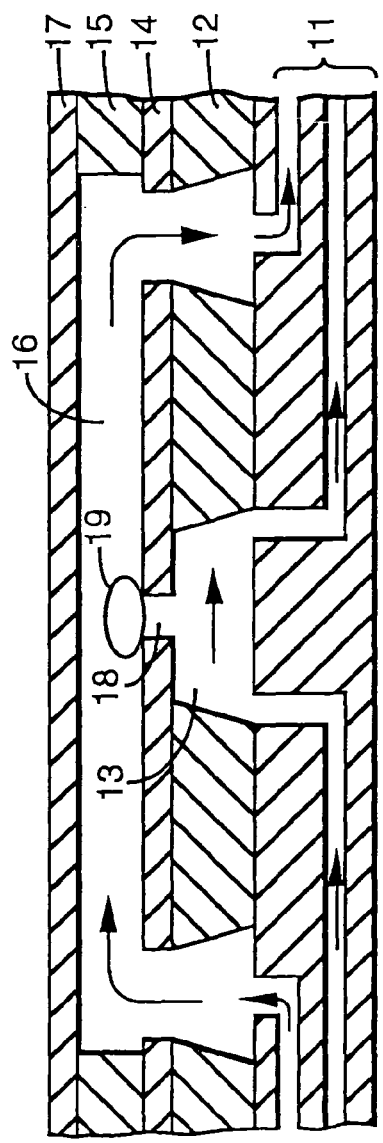
FIG. 1 is a cross section of a microdiffusion device useful in the practice of the present invention for infusing a biological cell with a chemical species without the assistance of an electrical current to effect electroporation.

While this invention extends to a variety of structures, methods, and applications, this portion of the specification will illustrate certain specific structures and methods in detail, from which the concepts of the invention as a whole will become apparent.

The first structure that will be discussed is an electroporation cell with an internal support to hold a single biological cell and an internal barrier that restricts the electric current flow in the electric cell to a flow path that passes through the biological cell. When no voltage is applied, the structure can be used for diffusive transport alone, unassisted by voltage-induced pore formation.

The configuration of the barrier, and the two chambers in embodiments that include two chambers, is not critical to the invention, and can vary widely while still serving the purposes and advantages of the invention. Since biological cells are microscopic in size, however, the preferred type of apparatus for the practice of this invention in each of its various forms is one in which the structure as a whole and/or its chambers are the size of electronic chips, fabricated by microfabrication techniques such as those used in electronic chip manufacture. It is further preferred that the chambers are constructed as flow-through chambers to allow the passage of the liquids in continuous flow, intermittent flow, or flow at the direction of the user, and to allow changes in the concentrations, pressure, and other conditions as needed to achieve close control over the passage of species across the biological cell membrane. Accordingly, a preferred structure and method of manufacture of the apparatus are those that involve the formation of the apparatus in layers or platelets with appropriate openings that form flow passages when the layers or platelets are bonded together.

Flow-through chambers offer the advantage of permitting the successive entry and removal of individual cells so that large numbers of cells can be treated in succession. Flow-through chambers also permit replenishment of solute-depleted solutions so that concentration gradients can be continuously maintained when desired. A further function that can be served by flow-through chambers is the increase and decrease of pressure, a function that is useful for various purposes as described below.

The support for the biological cell in this structure can be any structure that secures the biological cell in a fixed position and that allows the passage of electric current. The most convenient support is an opening in the barrier. Securement of a biological cell over the opening serves to close, seal or plug the opening, thereby directing the passage of electric current, diffusive transport, or both, through the cell and eliminating or minimizing leakage around the cell. A convenient mechanical means of achieving this is to impose a pressure differential across the opening in a direction that will press the cell against the opening. The diameter of the opening will be smaller than that of the cell, and the cell upon entering the apparatus will pass into one of the two chambers. By increasing the pressure in the chamber in which the cell resides, or lowering the pressure in the other chamber, the cell will be forced against the opening, closing it off. Once the procedure is completed, the cell is readily released from the opening by equalizing the pressures in the two chambers or by reversing the differential such that the higher pressure is in the chamber other than the chamber in which the cell was introduced. The flow of liquid in the chamber in which the cell was introduced will then remove the cell from the opening, exposing the opening for another cell.

An alternative method of sealing the opening with the cell is by the use of a coating on the barrier surface, or over the rim of the opening, of a substance that binds to the cell membrane. Since biological cell membranes are negatively charged, the coating may be a substance that bears a positive charge, such as polylysine, polyarginine, or polyhistidine. The biological cell can be directed to the opening by a pressure differential across the opening, and held in place by the coating. One the procedure is completed, the cell can be released from the coating by momentarily increasing the flow rate of the liquid in the chamber on the cell side of the opening, or by imposing a reverse pressure differential across the opening to urge the cell away from the opening.

The size of the opening is not critical to the invention provided that the opening exposes sufficient surface area on the cell membrane to achieve the desired degree of either mass transfer, the passage of an electric current, or both, within a controllable and economically reasonable period of time. The optimal size will thus vary with the particular cells being treated or studied. In general, the opening is preferably circular or approximately circular in shape, and depending on the cell size, preferably ranges in diameter from about 1 micron to about 100 microns, more preferably from about 1 micron to about 50 microns, and most preferably from about 2 microns to about 20 microns. The barrier in which the hole is formed and which separates the two chambers is preferably of a rigid dielectric material that is impermeable to both water and solutes and that will hold a pressure differential sufficient to secure a cell against the opening. For devices that are manufactured by microfabrication techniques, a convenient material for the barrier is silicon nitride. Other materials that will serve equally well will be readily apparent to those skilled in the art.

A further feature of preferred embodiments of this invention is the use of apparatus made of transparent materials. This enables the user to observe cell interiors and the processes of microdiffusion and microelectroporation through a microscope as they occur.

An example of a microdiffusion apparatus in accordance with this invention for a single biological cell, for transporting materials across the cell membrane without the application of an electric field, is shown in FIG. 1. This components of this apparatus, from the bottom up, are an acrylic base 11, an intermediate silicon layer 12 (1 micron in thickness) with a portion 13 carved out to define the lateral boundaries of the lower of the two liquid chambers, a silicon nitride layer 14 serving as the barrier between the two chambers, a silicon washer 15 defining the lateral boundaries of the upper liquid chamber 16, and a glass cover plate 17. A hole 18 in the silicon nitride barrier serves as the opening, and a cell or contiguous cell mass such as tissue 19 is shown covering the hole. Channels extend through the acrylic base to serve as inlet and outlet channels for the liquids that pass through the upper and lower chambers, as shown by the arrows in the Figure.

When the pressure in the upper chamber 16 is higher than that in the lower chamber 13, the cell will be retained in position over the hole, serving as a plug separating the liquids in the two chambers from each other. When the composition of the solutions in the two chambers differs from that of the cell interior, mass transfer occurs across the cell membrane between the chambers and the cell. When the composition of the solution in one chamber differs from that in the other, mass transfer occurs through the cell from one chamber to the other. By precisely controlling the compositions of the solutions in the two chambers, one can precisely control the mass transfer rate and direction within the cell. Since the diameter of the opening 18 is known, one can precisely determine the mass transfer that occurs through the opening.

The numerous applications of this microdiffusion device will be readily apparent. For example, the device can be used to infuse a cell with a cryopreservative such as glycerol by filling the upper chamber 16 with physiological saline and the lower chamber 13 with glycerol. When using a cell 19 for which the mass transfer coefficient of glycerol across the cell membrane is known, one can readily calculate the amount of glycerol that will enter the cell and adjust the concentrations and exposure times to infuse the cell with the amount that is known to be required for cryopreservation.

Figure 2:
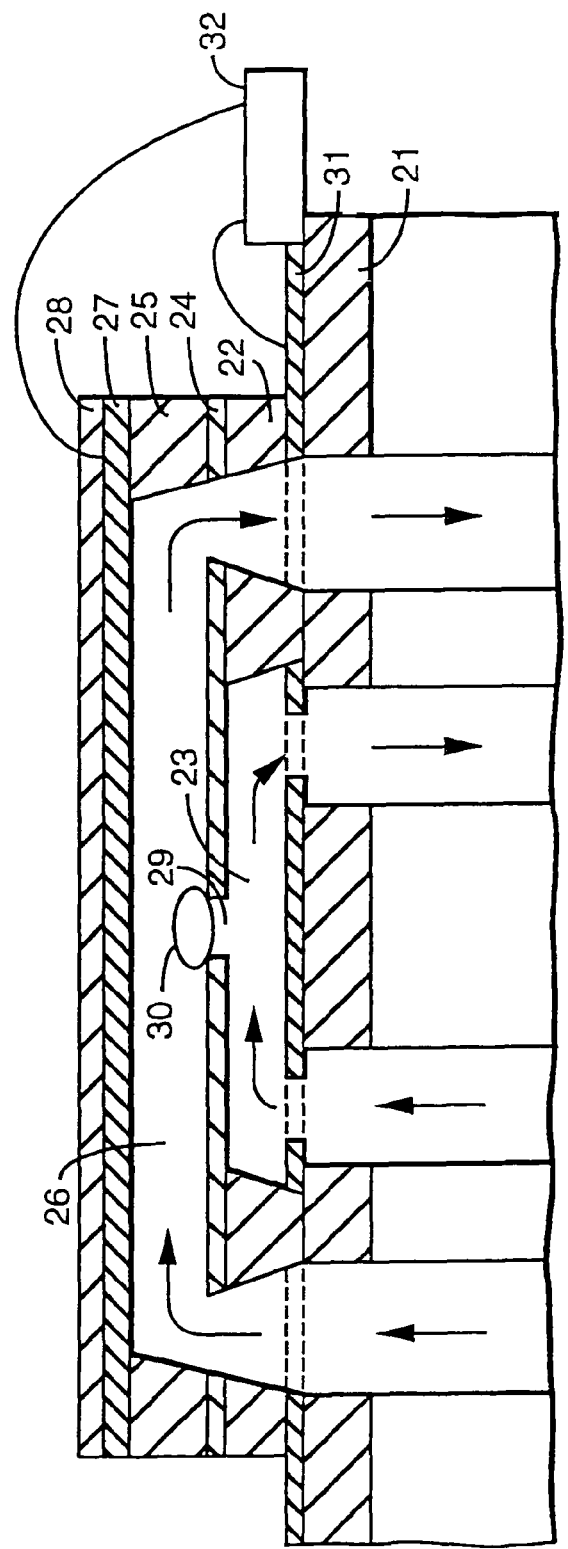
FIG. 2 is a cross section of a microelectroporation device useful in the practice of the present invention for achieving pore formation in a biological cell, and optionally for infusing the cell with a chemical species with the assistance of electroporation.

An example of a microelectroporation apparatus in accordance with this invention for a single biological cell, is shown in FIG. 2. The apparatus is similar in construction to the microdiffusion apparatus of FIG. 1. Its structural components, from the bottom up, are an acrylic base 21, a lower silicon layer 22 with a portion carved out to define the lateral boundaries of the lower liquid chamber 23, a silicon nitride layer 24 (1 micron in thickness) serving as the barrier between the two chambers, an upper silicon layer 25 defining the lateral boundaries of the upper liquid chamber 26, and a cover consisting of an n+ poly-silicon layer (5,000 Å in thickness) 27 and a silicon nitride layer (1 micron in thickness) 28. A hole 29 in the silicon nitride barrier 24 serves as the opening, and a cell 30 (or cell mass) covers the hole. Channels extend through the acrylic base to serve as inlets and outlets for the liquids that pass through the upper and lower chambers, as shown by the arrows in the Figure. A further layer of n+ poly-silicon (5,000 Å) 31 resides above the acrylic base 21, and this layer, together with n+ poly-silicon layer 27 above the upper chamber 26 serve as the two electrodes. Each electrode is joined by electric leads to a printed circuit board 32 which controls the voltage applied between the electrodes and measures the current passing between them.

The microelectroporation apparatus shown in FIG. 2 can be fabricated by conventional microfabrication techniques, typically involving chemical vapor deposition, masking, etching and sputtering. The operation of the apparatus will be analogous to the operation of the microdiffusion apparatus of FIG. 1. The movement of biological cells through the apparatus is achieved by suspending the cells in the liquid used to fill the upper chamber, and cells are drawn to the opening, one at a time, by imposing a pressure differential between the chambers, which also holds a cell in place once the cell has been drawn to the opening. A convenient method of imposing such a pressure differential is to maintain atmospheric pressure in the upper chamber while lowering the pressure in the lower chamber below atmospheric by attaching a syringe to the lower chamber and pulling on the syringe plunger. Care should be taken to limit the pressure differential to one that will not damage the cell.

Figure 3A:
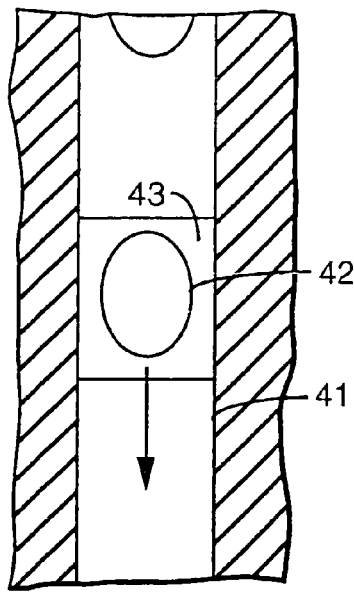
FIG. 3a is a longitudinal cross section of an electroporation device in accordance with this invention, designed for a mobile suspension of biological cells.
Figure 3B:
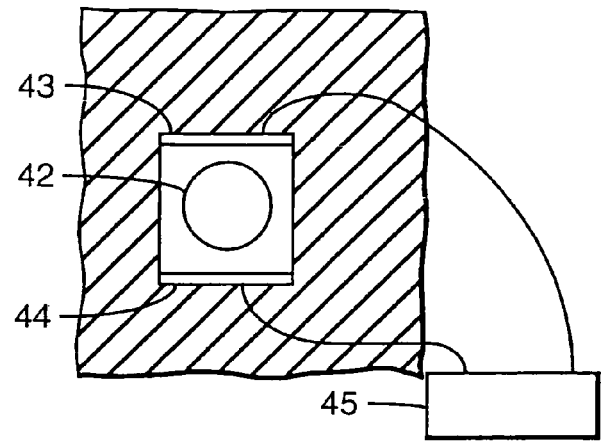

FIGS. 3a and 3b illustrate to a different apparatus and method within the scope of this invention. This apparatus and method involve a fluid suspension of biological cells flowing through a conduit or flow channel, in which the cells pass through a region between a pair of electrodes. The longitudinal cross section of FIG. 3a shows the walls 41 of the channel, and a biological cell 42 passing downward through the lumen of the channel (in the direction of the arrow). The transverse cross section of FIG. 3b shows that the channel is rectangular in cross section, although other cross-sectional geometries may be used. Electrodes 43, 44 are formed as coatings on two opposing walls of the channel. The electrodes are connected through leads to a printed circuit board 45 which measures the impedance and controls the voltage applied to the electrodes. The biological cell 42 is shown passing through the region between the two electrodes.

The area of the cross section of the channel is large enough to permit the cell to pass through essentially unimpeded by the channel walls, and yet small enough that only one cell can pass through the inter-electrode region at a time. In addition, each electrode 43, 44 is either approximately equal in length or slightly larger in length than the diameter of the biological cell, so that the cell upon entering the region causes a significant or measurable decrease in the current passing through the region due to the voltage applied across electrodes. The spacing of the electrodes, i.e., the distance between them, is likewise subject to the same considerations. The biological cells are suspended in a liquid solution of the species to be introduced into the cells, and the suspension is passed through the channel. A voltage is applied between the electrodes as suspension flows through the channel, and the current between the electrodes (or the impedance) is monitored. A significant drop in the current indicates the presence of a biological cell in the inter-electrode region. Once the cell is detected in this manner, an electroporation pulse can be applied to the electrodes while the cell is still in the inter-electrode region, and impedance can be observed further to detect the onset of electroporation. The species dissolved in the liquid solution will enter the cell as a result of the electroporation.

Variations on these structures and methods will be readily apparent to those skilled in the art. For example, the barriers described above can be minimized or avoided by using microelectrodes that are the same size as or smaller than the biological cells. Examples of such microelectrodes are carbon fiber microelectrodes (such as ProCFE, Axon Instruments, Foster City, Calif., USA) used in conjunction with high-graduation micromanipulators (such as those available from Narishige MWH-3, Tokyo, Japan). Microelectrodes can be used in place of the electrodes shown in FIG. 2 or in place of those shown in FIGS. 3a and 3b.

The following examples are offered for illustration, and are not intended to impose limits on the scope of the invention.

EXAMPLE 1

A series of experiments was performed using a microelectroporation system consisting of the microelectroporation device described above and shown in FIG. 2, combined with flow and pressure control units and pressure gauges for the liquids to be circulated through the upper and lower chambers, a variable DC power supply, a pulse generator and power amplifier for imposing voltage pulses across the device, a digital oscilloscope for monitoring the pulses, a fluorescent microscope, a CCD (charge coupled device) camera, and a computer with image processing and waveform processing software. Both chambers of the device were filled with physiological saline and cells were introduced into the upper chamber. Liquid motion in the top and bottom chambers was controlled by syringes. The pressure in the upper chamber was atmospheric while the pressure in the lower chamber was reduced below atmospheric by pulling on the barrel of the syringe connected to that chamber. The voltage was applied in single square pulses ranging from zero to 120V in magnitude and from 2 microseconds to 100 milliseconds in duration. The distance between the electrodes in the upper and lower chambers was 900 microns.

The tests in this example were performed using ND-1 human prostate adenocarcinoma cells with a typical diameter of 20 microns. The opening in the microelectroporation device was 5 microns in diameter. A rectangular voltage pulse was applied with a duration of 60 milliseconds, and the pulse was applied at various amplitudes ranging from 10V to 60V in increments of 5 volts. With each pulse, the electric current passing through the opening was measured. Experiments were performed with the cells and were repeated both with the opening stopped by a glass bead and with no obstruction at all in the opening. The results in each case were expressed as microamperes of current vs. volts of pulse amplitude and are plotted in FIG. 4, in which the upper curve (data points represented by x's) represents the unobstructed opening, the lower curve (data points represented by asterisks) represents the data taken with the glass bead residing in the opening, and the three middle curves (open squares, open upright triangles, and open inverted triangles) represent data taken with three different ND-1 cells residing in the opening.

The upper curve shows that the current increases in a substantially steady manner as the voltage increases when there is no barrier to the passage of current through the opening. The lower curve also shows a substantially steady rise as the voltage increases, although at a much lower level. The current values shown in the lower curve represent stray currents through the device. The curves of data taken with the ND-1 cells across the opening show that at low voltages the current is close in value to that obtained when the opening is closed by the glass bead while at high voltages the current rises to the levels obtained with an unobstructed opening. The transition is a sharp increase which is indicative of the formation of pores in the cell membrane through which an electric current can pass, i.e., the onset of electroporation. In all three cells, the transition occurred at voltages between 30V and 40V. In two of the three cells (open squares and open upright triangles), the onset of electroporation occurred essentially at the same voltage, while in the third (inverted triangles), the onset occurred at a voltage that was lower than the other two by about 5V. This illustrates the value of controlling the process for individual cells to achieve optimal results.

Figure 4:
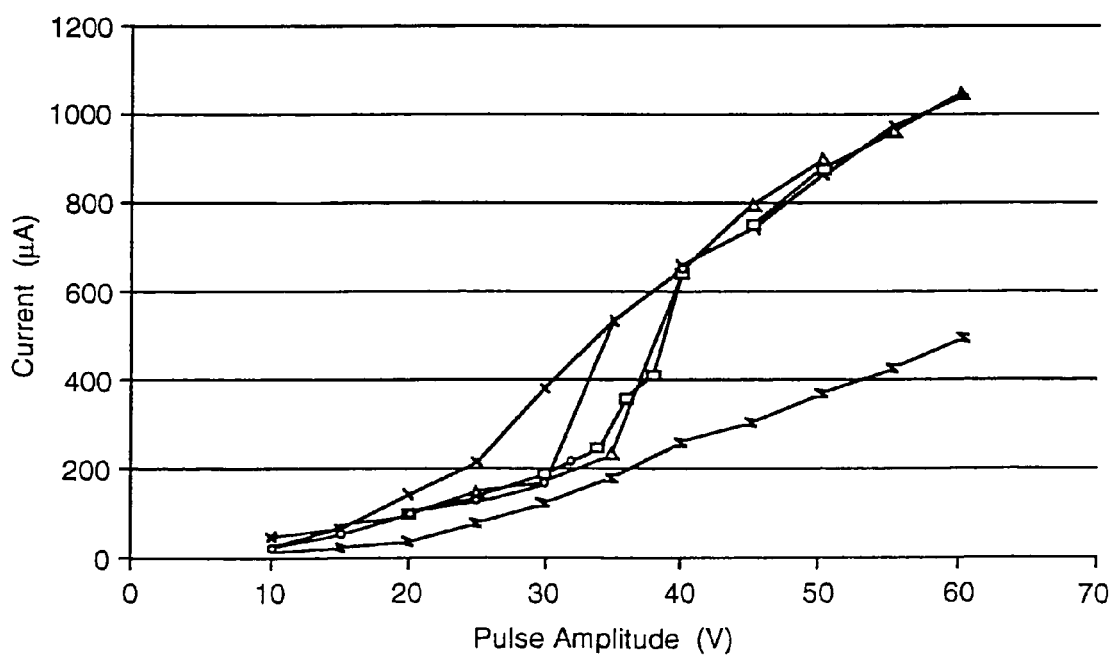
FIG. 4 is a plot of current vs. voltage in a series of electroporation experiments conducted using a microelectroporation device of the structure similar to that of FIG. 2.

After the data shown in FIG. 4 was generated, the pulses were reapplied in descending order of amplitude values, and the resulting curves displayed hysteresis, i.e., the curves obtained with descending amplitudes were higher in voltage than those obtained with ascending amplitudes. This indicated that the electroporation in these experiments was irreversible.

EXAMPLE 2

Using the same microelectroporation system used in Example 1, a series of tests were performed on rat hepatocytes (ATCC #CRL-1439), whose typical cell diameter was 20 microns, the microelectroporation apparatus having an opening that was 4 microns in diameter. Here as well, rectangular voltage pulses that were 60 milliseconds in duration were used, ranging in amplitude from 10V to 37.5V in increments of 5V in the portion from 10V to 30V and in increments of 2.5V in the portion from 30V to 37.5V. The experiments were performed in some cases only by increasing the amplitudes and in others by first increasing, then decreasing the amplitudes to evaluate reversibility. The results are plotted in the graphs shown in FIGS. 5a, 5b, 5c, and 5d. In each case, the upper curve (data points represented by circles) is the data taken with neither a cell nor a glass bead residing in the opening, the lower curve (data points represented by squares) is the data taken with a glass bead in the opening, and the middle curve (data points represented by triangles) is the data taken with a hepatocyte in the opening, using different hepatocytes for each of the four Figures.

Figure 5A:
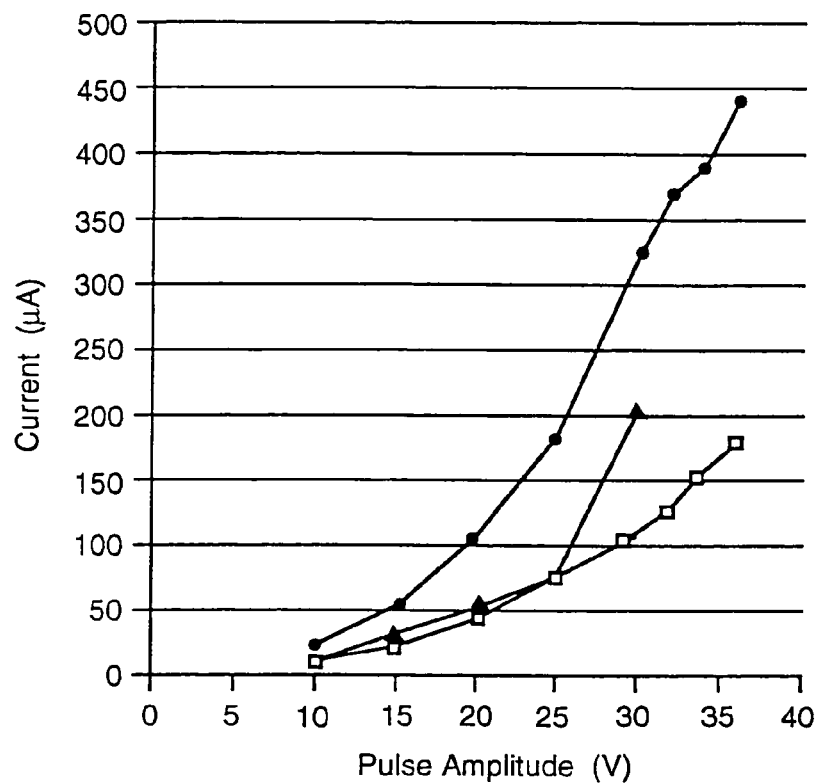
FIGS. 5a, 5b, 5c, and 5d are plots of current vs. voltage in a further series of electroporation experiments conducted using a microelectroporation device similar to that of FIG. 2.
Figure 5B:
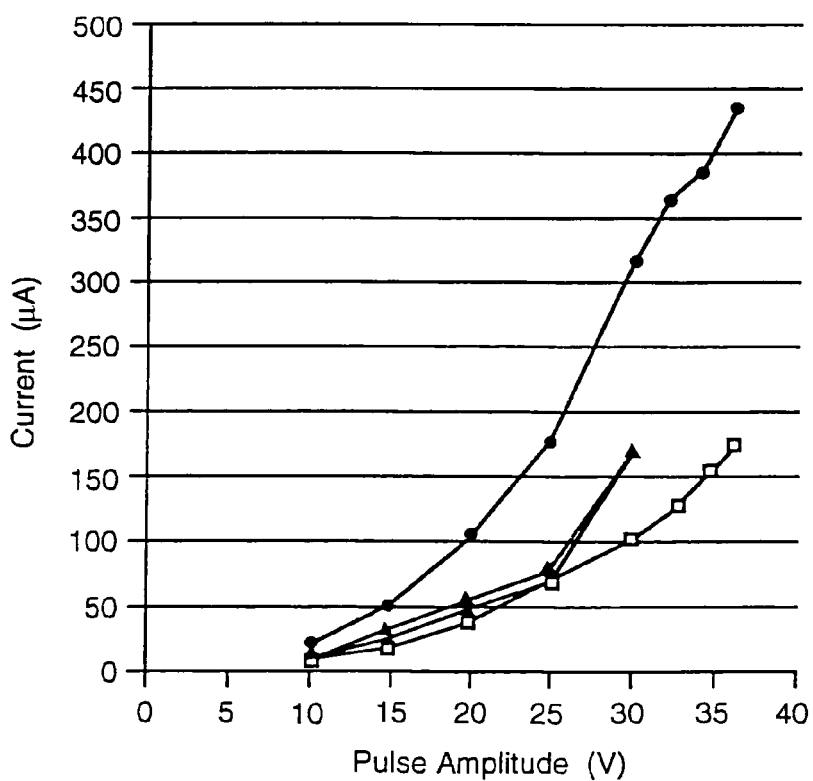
Figure 5C:
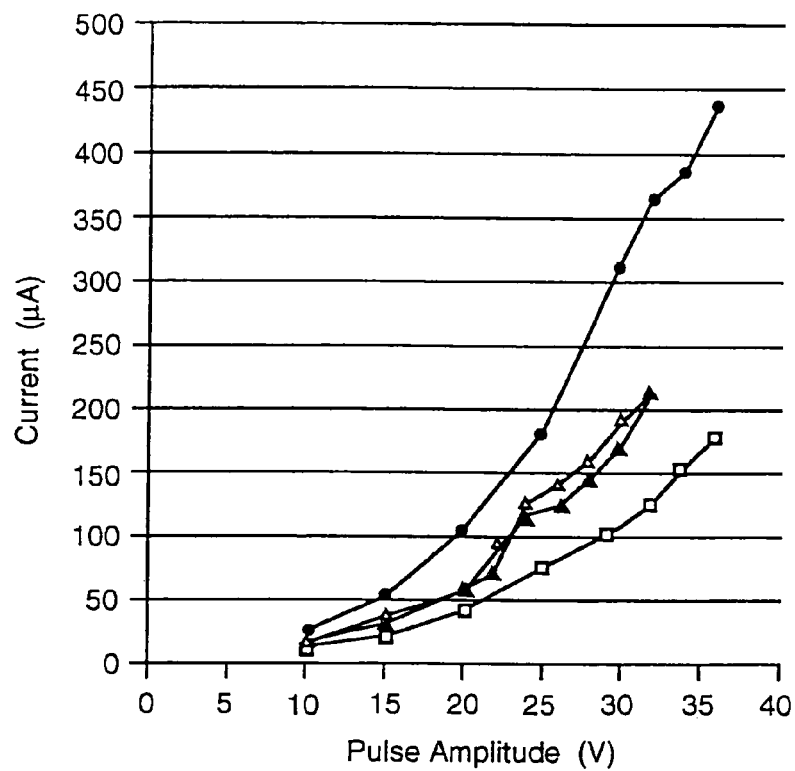
Figure 5D:
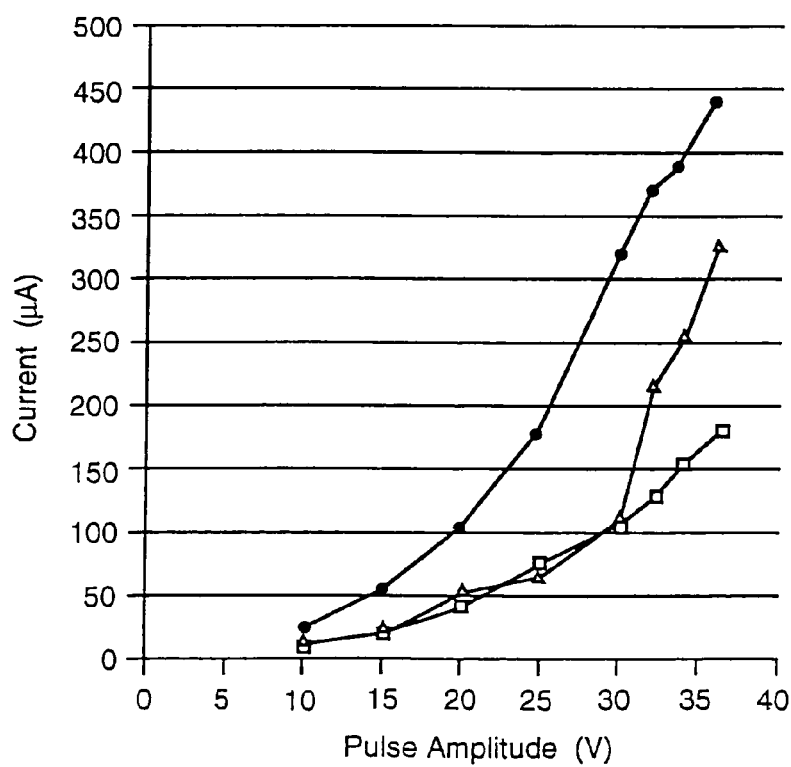

In FIG. 5a, the amplitude was increased and not decreased, displaying an electroporation threshold voltage of between 25V and 30V. In FIGS. 5b and 5c, the amplitude was first increased and then decreased to produce the two middle curves. Although the ascending and descending curves are not differentiated, they are substantially identical in each Figure, indicating that the cell membrane in each of these two cases resealed after each voltage pulse and thus that the pore formation was reversible. In the test represented by FIG. 5d, the cell disintegrated once the applied voltage-exceeded 37.5V, although this is not shown in the Figure. It is significant to note that despite the fact that the same cell types were used in each of FIGS. 5a, 5b, 5c, and 5d, the electroporation threshold voltage differed among the individual cells, although all were within the range of 20V to 35V. Adaptation of the procedure to individual cells is readily achieved by monitoring the current in this manner to note when the electroporation threshold occurs. Selection of the optimal exposure time, voltage, composition changes in the surrounding liquids, and other parameters of the system can then be made to achieve the desired treatment of the cell without destruction of the cell.

The methods described herein are useful tools in the laboratory for conducting fundamental research in the electroporation properties of biological cells, and useful tools in industry for processing large quantities of cells in a flow-through manner. By enabling one to observe and record the current flowing through individual cells, one can control the amplitude and duration of the voltage pulse to achieve optimal results. In addition, the devices described and shown herein for use in practicing the invention can be constructed with transparent parts and of a size suitable for mounting on a microscope stage. This will permit one to correlate the electrical current measurements to visual observations and fluorescence measurements inside the cell. The device can be used to electrically detect, through the measurement of currents, the point in time when a cell becomes lodged in the opening as well as the point in time when pore formation is achieved in the cell membrane. For larger scale and industrial applications, large numbers of microelectroporation devices of the type described herein can be arranged in parallel. For each cell, electrical information indicating the trapping of a cell in the opening (such as a sharp drop in the current) can be used to generate a signal that will initiate an electroporation sequence, and further electrical information indicating the completion of electroporation (such as a sharp rise in current) will generate a signal that will release the cell (for example by eliminating or reversing the pressure differential) and permit the next cell to flow toward the opening.

Further implementations, applications, adaptations, and embodiments of the concepts, features and methods described herein that are within the scope of this invention will be readily apparent to those skilled in the art.

What is claimed is:

1. A method of electroporating a cell mass in a controlled manner, the method comprising:
   (a) applying a voltage across a cell mass;
   (b) detecting the ratio of electric current through the cell mass to the voltage applied across the cell mass, wherein a change in the ratio indicates a change in the degree of electroporation of the cell mass;
   (c) determining an irreversible electroporation voltage for the cells of the cell mass, wherein the determining of the irreversible electroporation voltage comprises determining an electroporation current-to-voltage onset point of the cell mass or an electroporation current-to-voltage hysteresis of the cell mass; and
   (d) adjusting the applied voltage to provide the determined irreversible electroporation voltage of step (c), thereby providing an irreversible electroporation of the cells of the cell mass.

2. The method of claim 1, wherein in step (c) the determining of the irreversible electroporation voltage further comprises continuously detecting a current-to-voltage ratio in the cell mass, and wherein in step (d) the adjusting further comprises adjusting the applied voltage for a duration of time sufficient to provide a controlled, irreversible electroporation of cells of the cell mass.

3. The method of claim 1, wherein the cells are human prostate cancer cells.

4. The method of claim 1, further comprising:
   (e) positioning a barrier having an opening wherein the positioning of the barrier comprises trapping the cell mass in the opening of the barrier, thereby causing the electrical current to flow through the trapped cell mass.

5. A method of electroporating a biological cell sample in a controlled manner, the method comprising:
   (a) applying a voltage across a biological cell sample;
   (b) detecting changes in electrical impedance occurring across the biological cell sample, wherein said changes in electrical impedance are caused by the applied voltage electroporating cells in the biological cell sample;
   (c) calculating from the changes in electrical impedance obtained from step (b) an amount and a duration of a voltage to obtain a change in electrical impedance; and
   (d) from the amount and duration of voltage calculated in step (c), applying an amount and a duration of a voltage sufficient to obtain a controlled, irreversible electroporation of the cells of the biological cell sample.

6. The method of claim 5, wherein the biological cell sample is a tissue sample containing the biological cells and wherein the biological cells in the sample are human prostate adenocarcinoma cells.

7. The method of claim 5, further comprising:
   (e) positioning a barrier having an opening wherein the positioning of the barrier comprises trapping the cell sample in the opening of the barrier and wherein the applying the voltage causes the electrical current to flow through the trapped cell sample.

* * * * *